United States Patent [19]

Urban et al.

[11] Patent Number: 4,564,129
[45] Date of Patent: Jan. 14, 1986

[54] DOSAGE DISPENSING UNIT

[75] Inventors: Joseph J. Urban, Richboro, Pa.; Norman L. Henderson, Gladstone, N.J.

[73] Assignee: Hoechst-Roussel Pharmaceuticals Inc., Somerville, N.J.

[21] Appl. No.: 461,289

[22] Filed: Jan. 27, 1983

[51] Int. Cl.⁴ .............................................. B65D 37/00
[52] U.S. Cl. ................................... 222/207; 604/212; 222/454; 222/211; 239/327
[58] Field of Search ................ 604/212; 239/327, 121; 128/200, 22; 222/207, 209, 454, 455, 456, 584, 205

[56] References Cited

U.S. PATENT DOCUMENTS

| 1,798,067 | 3/1931 | Comstock | 222/584 |
| 2,583,821 | 1/1952 | DuBois | 239/327 |
| 2,616,593 | 11/1952 | Leibenhaut . | |
| 2,728,491 | 12/1955 | Aneshansley . | |
| 2,951,264 | 9/1960 | Bailey . | |
| 2,989,215 | 6/1961 | Willingham . | |
| 3,140,052 | 7/1964 | McCuiston . | |
| 3,269,389 | 8/1966 | Meurer et al. | 239/327 |
| 4,083,496 | 4/1978 | Oshima et al. . | |

FOREIGN PATENT DOCUMENTS

| 280820 | 4/1970 | Austria . | |
| 870151 | 3/1942 | France | 222/584 |
| 1397362 | 3/1965 | France | 222/454 |
| 1559542 | 1/1980 | United Kingdom | 222/454 |
| 2038779 | 7/1980 | United Kingdom . | |

Primary Examiner—H. Grant Skaggs
Attorney, Agent, or Firm—Raymond R. Wittekind

[57] ABSTRACT

A dosing unit for delivering a measured dosage includes a dosage well positioned on the inside wall of a spray tip or neck of a squeeze bottle, a fill trough for filling the well upon tilting of the bottle in any direction, and a spray tip for delivery of the dosage which includes an orifice and a flow tube extending from the bottom of the dosage well to the spray orifice. The well may be either molded into a spray tip or molded into the neck of the bottle or a molded insert that fits into the spray tip or bottle neck.

6 Claims, 7 Drawing Figures

DOSAGE DISPENSING UNIT

BACKGROUND OF THE INVENTION

The present invention relates to dispensing units and pertains particularly to a metered dosage dispensing unit.

It is frequently desirable to dispense certain liquids in specific measured quantities from a bottle or container. For example, many liquid medications are prescribed in specific dosage quantities.

One prior art approach has been to provide a dosage well in a bottle or container so that specific dosages can be administered directly from the container by a nozzle or orifice without the use of external measuring and/or administering instruments. The problem with many prior art devices is that the container or bottle must be carefully tilted in the precise direction of the dosage well in order to fill the well with the defined dosage.

The present invention is directed to an improved dosage dispensing unit which overcomes the aforementioned problem in prior art devices.

SUMMARY AND OBJECTS OF THE INVENTION

It is the primary object of the present invention to provide an improved measured dosage dispensing device.

In accordance with the primary aspect of the present invention, a dosage dispensing device includes a dosage well positioned within a spray tip, or the neck of a bottle, or a molded insert that fits into a spray tip or bottle neck, with a fill trough communicating with the well for receiving and channeling liquid into the well upon tilting of the bottle in any direction.

BRIEF DESCRIPTION OF THE DRAWINGS

The above and other objects and advantages of the present invention will become apparent from the following description when read in conjunction with the accompanying drawings wherein:

Referring to FIG. 1, a dosage dispensing unit designated generally by the numeral 10 is shown mounted on a container or bottle 12 in position in the open neck 14 thereof. The dispensing unit 10 is designed to fit within the open neck of a conventional bottle. The bottle 12 is preferably a resilient or elastic squeeze bottle that may be molded or otherwise fabricated of a resilient plastic material such as polyethylene or polypropylene. The bottle 12 serves both as a packaging container and also as a squeezable bulb with which to produce and apply the necessary fluid pressure to dispense the liquid from the container.

Figure 2:
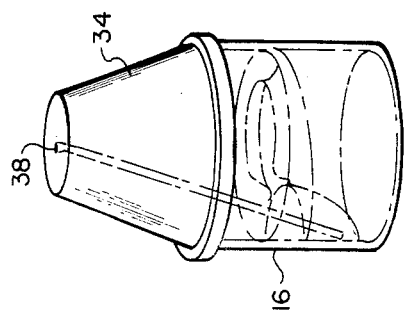
FIG. 2 is a perspective view of the dosage unit of FIG. 1.
Figure 3:
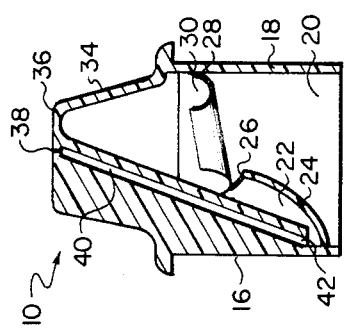
FIG. 3 is a section view of the unit of FIG. 2.

The dosage dispensing unit as shown in FIGS. 2 and 3 includes a generally cylindrical body portion 16 designed to fit within a generally cylindrical container opening (e.g. 14) and be secured in place in any suitable manner such as by gluing, welding, friction fit, threads, etc. The unit may be inserted in place in the container after the container has been filled at the factory and further sealed by a cap not shown. The cylindrical body portion 16 is defined by an annular cylindrical wall 18 forming an inner, substantially cylindrical chamber 20 which is open at the lower end for communicating with the interior of the bottle or container 12.

A metering dosage well 22 is formed on one side of the chamber on the interior side of wall 18 within chamber 20 by means of a wall 24 extending and curving outwardly and upwardly from a closed bottom to an open top. The well is designed to hold a pre-determined measured quantity of liquid. An overflow depression 26 formed in the top edge of the wall 24 spills excess liquid from the well 22 and allows air to escape from the well 22 thereby permitting complete filling of the well 22 by liquid upon tilting of the bottle 12 containing the liquid.

Figure 1:
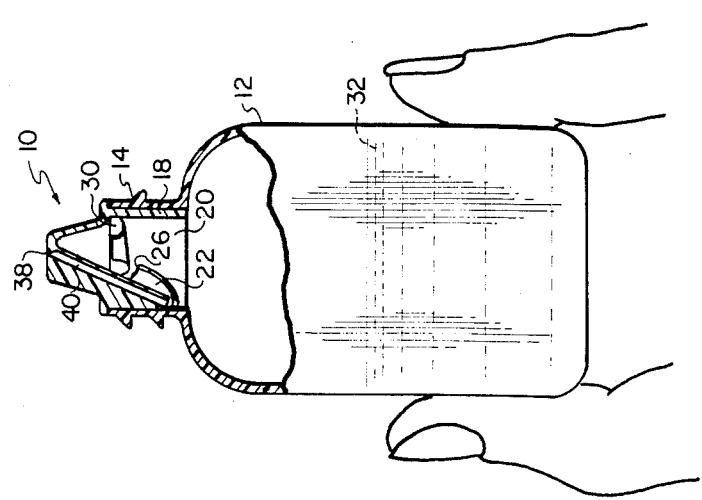
FIG. 1 is a side elevation view, partially in section, showing a preferred embodiment of the dosage unit in position in the neck of a bottle.

A semi-annular fill trough or channel 28 formed by curved wall 30 extends around the inside of wall 18 just above well 22 and slopes downward from the side opposite the well toward the well with both ends of the trough opening into the well. This fill trough catches liquid and channels it toward the well 22 regardless of the direction of tilt of the container 12. For example, if the container is tilted 90 degrees to the right away from well 22 as viewed in FIGS. 1 and 3 and then tilted back upright, liquid 32 within the container will be caught by trough 28 and forced to flow into well 22 with excess liquid spilling over the overflow depression 26. This provides a pre-determined quantity (dosage) of liquid to be dispensed from the well.

The dispensing unit 10 includes a dispensing tip suitably shaped with a tapered outer wall 34 and end 36 for use in dispensing nasal spray for example. A dispensing orifice 38 opens into a dispensing tube 40 having its lower end 42 extending into and down to the bottom of dosage well 22. The dispensing unit may be utilized for dispensing any number of substances and the dispensing nozzle may be designed accordingly.

In use, a container having a quantity of the desired liquid substance and appropriate dosage dispensing unit is selected. When it is desired to discharge a measured amount of the liquid, the container is tilted on its side in any direction and then righted. This tilting action loads the dosage well with the measured dosage ready to dispense. The tip 34, 36 is then inserted into the appropriate body orifice and the container 12 squeezed until all liquid is forced from the well 22 via tube 40 and air begins to be expelled from the dispensing orifice 38. When the liquid charge has been dispensed, the squeezing pressure is relieved and the container returns to its typical configuration.

Figure 4:
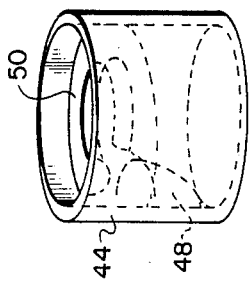
FIG. 4 is a perspective view of an alternate embodiment.
Figure 5:
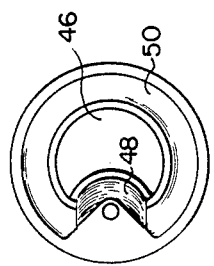
FIG. 5 is a top view of the unit of FIG. 4.

Referring to FIGS. 4 and 5, an alternate embodiment is illustrated wherein the dosage measuring unit is constructed as a separate unit 44 having a cylindrical outer configuration for fitting within the usual cylindrical bottle neck. The unit is otherwise constructed with an inner chamber having a dosage well 48 and dosage well fill trough 50 as in the prior embodiment. A suitable dispensing tip may be separately fabricated by molding or the like and assembled on the dosage measuring unit.

Figure 6:
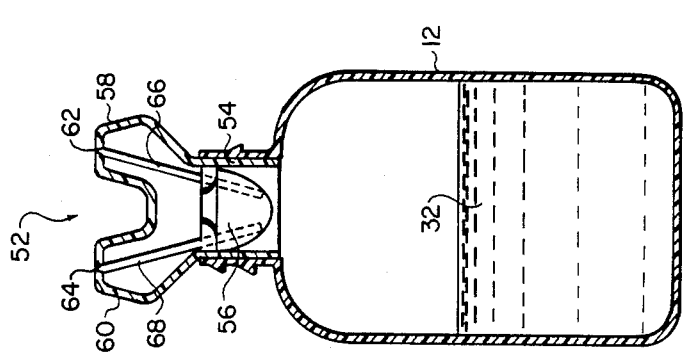
FIG. 6 is a front elevation view in section of a further embodiment of the dispensing unit.

Referring to FIG. 6, an alternate dispensing tip 52 is illustrated mounted in the bottle 12. The dispensing unit includes a cylindrical portion formed by annular walls 54 and including a dosage well 56 formed on the side wall as in the prior embodiments. A fill trough is formed around the interior wall 54 for emptying into the dosage well 56. A pair of spaced apart protruding tips 58 and 60 extend upward from the unit and include a pair of nozzles or orifices 62 and 64 communicating via flow tubes 66 and 68 with the bottom of the dosage well 56. These tubes may be separate tubes as illustrated or they may be passages molded in the cap as in the previous embodiments.

Figure 7:
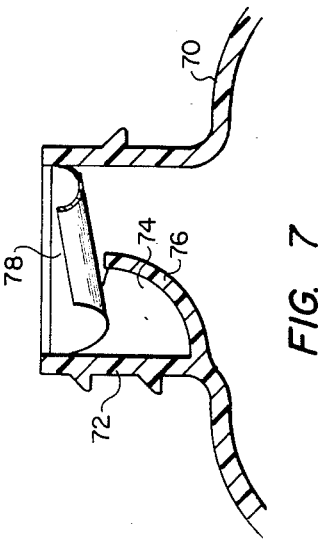
FIG. 7 is an enlarged view in section of still another embodiment of the dosage unit.

Referring to FIG. 7, a still further modification is illustrated wherein a bottle 70 is molded with a dosage well 74 formed in the inside of the neck 72. The dosage well 74 is defined by a wall 76. A semi-circular fill trough 78 is also formed in the neck 72 just above the dosage well 74. Where special use bottles are made primarily as dispensing bottles of this character, this portion of the dispensing unit may be preferably molded into the bottle. A dispensing tip of the desired configuration may then be added.

While we have illustrated and described our invention by means of specific embodiments, it should be understood that numerous changes and modifications may be made therein without departing from the spirit and scope of the invention as defined by the appended claims.

What is claimed is:

1. A dosage dispensing unit for attachment to a container, said unit comprising:
    a cylindrical body member for attachment to the open mouth of a bottle, said member having a cylindrical chamber defined by an interior wall and being open at one end for communicating with the interior of the bottle, said cylindrical chamber also communicating with a dispensing outlet,
    a dosage well formed on one side of the interior wall of said body member, said well being formed by a wall extending upwardly from the lower portion of the cylindrical body, and being open at the top and closed at the bottom,
    a semi-annular trough extending around said interior wall, the inner surface of the trough defining a communicating channel between the interior of the bottle and the upper surface of the trough, and communicating at both ends thereof with said dosage well for receiving liquid upon tilting of said bottle and channeling same to said dosage well, and
    an overflow depression defined by the upper edge of the wall of the well and the communicating channel, which depression allows air to escape from the well upon filling with liquid.

2. The dosage unit of claim 1 wherein said trough is inclined toward said dosage well.

3. The dosage unit of claim 2 including a spray tip on said unit, said spray tip wherein said dispensing outlet includes a pair of spray nozzles and a delivery tube for communicating liquid from said dosage well to each of said nozzles.

4. The dosage unit of claim 1 wherein said dispensing outlet includes a spray tip on said unit, said tip comprising a spray orifice and a tube connected to said orifice, said tube extending into said dosage well for communicating liquid from said well to said spray orifice.

5. The dosage unit of claim 3 in combination with a resilient squeeze bottle.

6. A dosage dispensing unit for dispensing a measured dosage from a squeeze bottle, said dispensing unit comprising:
    a cylindrical body member having an outer end and an inner end for attachment to the open mouth of an elastic squeeze bottle, said body member having a cylindrical chamber defined by an interior wall having an open end for communicating with the open mouth of a squeeze bottle;
    a dosage well formed on one side of the interior wall of said body member, said well being formed by a well extending upwardly from the lower portion of the body member and being open at the top and closed at the bottom;
    a semi-annular trough extending around said interior wall, the inner surface of the trough defining a communicating channel between the interior of the bottle and the upper surface of the trough and communicating at both ends thereof with said dosage well for receiving liquid upon tilting of said bottle and channeling same to said dosage well;
    an overflow depression defined by the upper edge of the wall of the well and the communicating channel, which depression allows air to escape from the well upon filling with liquid;
    a dispensing orifice formed in said outer end of said body member; and
    a passage for communicating liquid from said dosage well to said dispensing orifice.

* * * * *